(12) United States Patent
Han et al.

(10) Patent No.: US 8,052,932 B2
(45) Date of Patent: Nov. 8, 2011

(54) POLYMER NANOFIBER-BASED ELECTRONIC NOSE

(75) Inventors: Li Han, Apex, NC (US); Anthony L. Andrady, Apex, NC (US); David S. Ensor, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 1282 days.

(21) Appl. No.: 11/615,285

(22) Filed: Dec. 22, 2006

(65) Prior Publication Data

US 2008/0150556 A1    Jun. 26, 2008

(51) Int. Cl.
*G01N 27/04* (2006.01)
*G01N 27/06* (2006.01)
*G01R 27/22* (2006.01)

(52) U.S. Cl. ........ 422/90; 422/82.02; 324/693; 977/957

(58) Field of Classification Search ............ 422/50, 422/68.1, 82.01, 82.02, 83, 88, 90; 977/700, 977/742, 744, 748, 762, 902, 932, 953, 957; 324/693

See application file for complete search history.

(56) References Cited

U.S. PATENT DOCUMENTS

| 7,592,277 | B2 | 9/2009 | Andrady et al. | |
|---|---|---|---|---|
| 7,687,276 | B2 * | 3/2010 | Kunz | 436/164 |
| 2003/0121887 | A1 | 7/2003 | Garvey et al. | |
| 2004/0217331 | A1 | 11/2004 | Lussey et al. | |
| 2005/0241935 | A1 | 11/2005 | Lewis et al. | |
| 2008/0113214 | A1 | 5/2008 | Davis et al. | |

OTHER PUBLICATIONS

X. Wang et al., Electrospun Nanofibrous Membranes for Highly Sensitive Optical Sensors, 2 Nano Lett. 1273-1275 (2002).*
R. Kessick & G. Tepper, Electrospun Polymer Composite Fiber Arrays for the Detection and Identification of Volatile Organic Compounds, 117 Sens. Actuators B 205-210 (2006).*
B. Sundaray et al., Electrical Conductivity of a Single Electrospun Fiber of Poly(Methyl Metacrylate) and Multiwalled Carbon Nanotube Composite, 88 Appl. Phys. Lett. 143114-1-143114-3 (2006).*
Y. Wang et al., A Convenient Route to Polyvinyl Pyrrolidone/Silver Nanocomposite by Electrospinning, 17 Nanotechnology 3304-3307 (2006).*
J. Huang et al., Polyaniline Nanofibers: Facile Synthesis and Chemical Sensors, 125 J. Am. Chem. Soc. 314-315 (2002).*

(Continued)

*Primary Examiner* — Glenn Caldarola
*Assistant Examiner* — Randy Boyer
(74) *Attorney, Agent, or Firm* — Oblon, Spivak, McClelland, Maier & Neustadt, L.L.P.

(57) ABSTRACT

A chemical sensor and a system and method for sensing a chemical species. The chemical sensor includes a plurality of nanofibers whose electrical impedance varies upon exposure to the chemical species, a substrate supporting and electrically isolating the fibers, and a set of electrodes connected to the plurality of fibers at spatially separated points to permit the electrical impedance of the plurality of fibers to be measured. The system includes the chemical sensor, an impedance measuring device coupled to the electrodes and configured to determine an electrical impedance of the plurality of fibers, and an analyzer configured to identify the chemical species based on a change in the electrical impedance. The method measures at least one change in an electrical impedance between spatially separated electrodes connected to a plurality of fibers upon exposure of the fibers to the chemical species, and identifies the chemical species based on the measured change in the electrical impedance.

57 Claims, 13 Drawing Sheets

Cross-Sectional View

Composite nanofiber sensing material 19a

Substrate 14

Printed Electrode 8

OTHER PUBLICATIONS

Z.-M. Huang et al., A Review on Polymer Nanofibers by Electrospinning and Their Applications in Nanocomposites, 63 Compos. Sci. Technol. 2223-2253 (2003).*

W. E. Teo and S. Ramakrishna, A Review on Electrospinning Design and Nanofibre Assemblies, 17 Nanotechnology R89-R106 (2006).*

S. Virji et al., Polyaniline Nanofiber Gas Sensors: Examination of Response Mechanisms, 4 Nano Lett. 491-496 (2004).*

H. Liu et al., Polymeric Nanowire Chemical Sensor, 4 Nano Lett. 671-675 (2004).*

Haifen Xie, Gas Sensor Arrays Based on Polymer-Carbon Black to Detect Organic Vapors At Low Concentration, Science Direct, Mar. 28, 2005, pp. 1-5.

U.S. Appl. No. 12/575,892, filed Oct. 8, 2009, Ensor, et al.

* cited by examiner

Cross-Sectional View

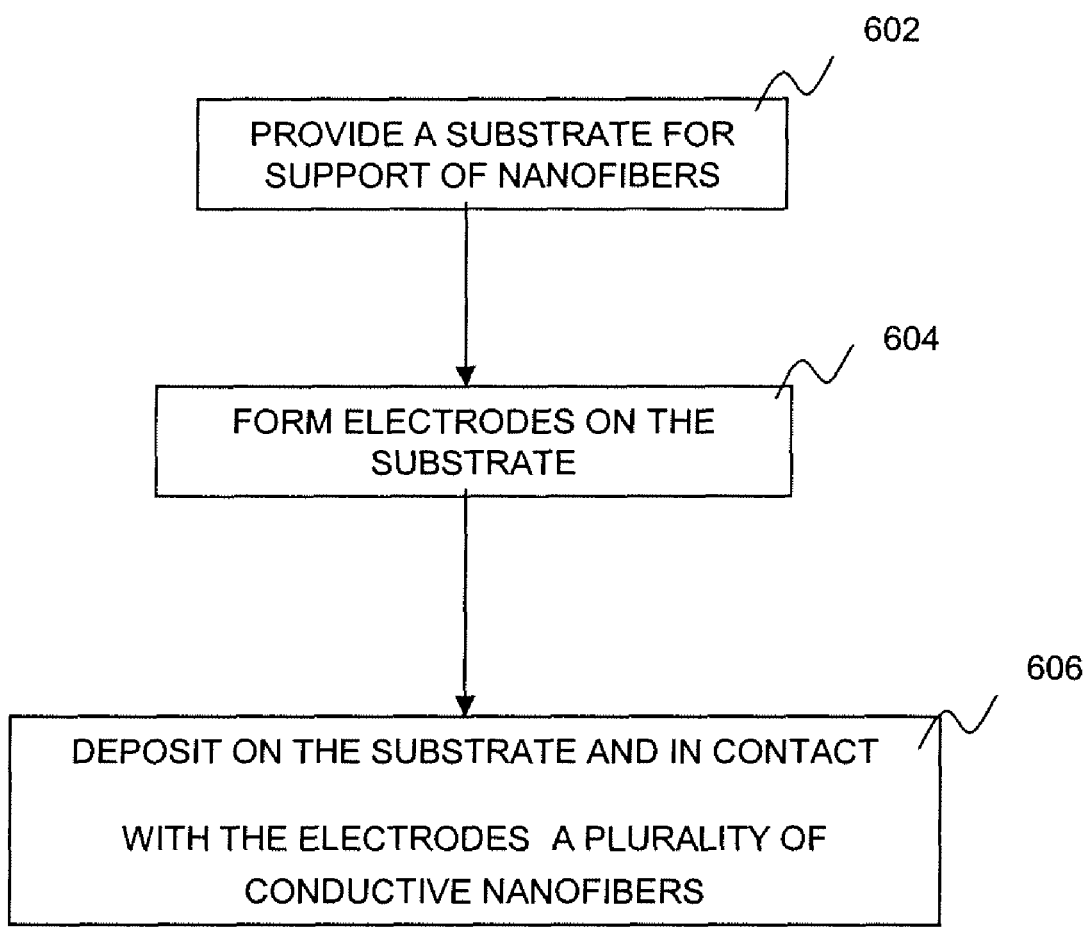

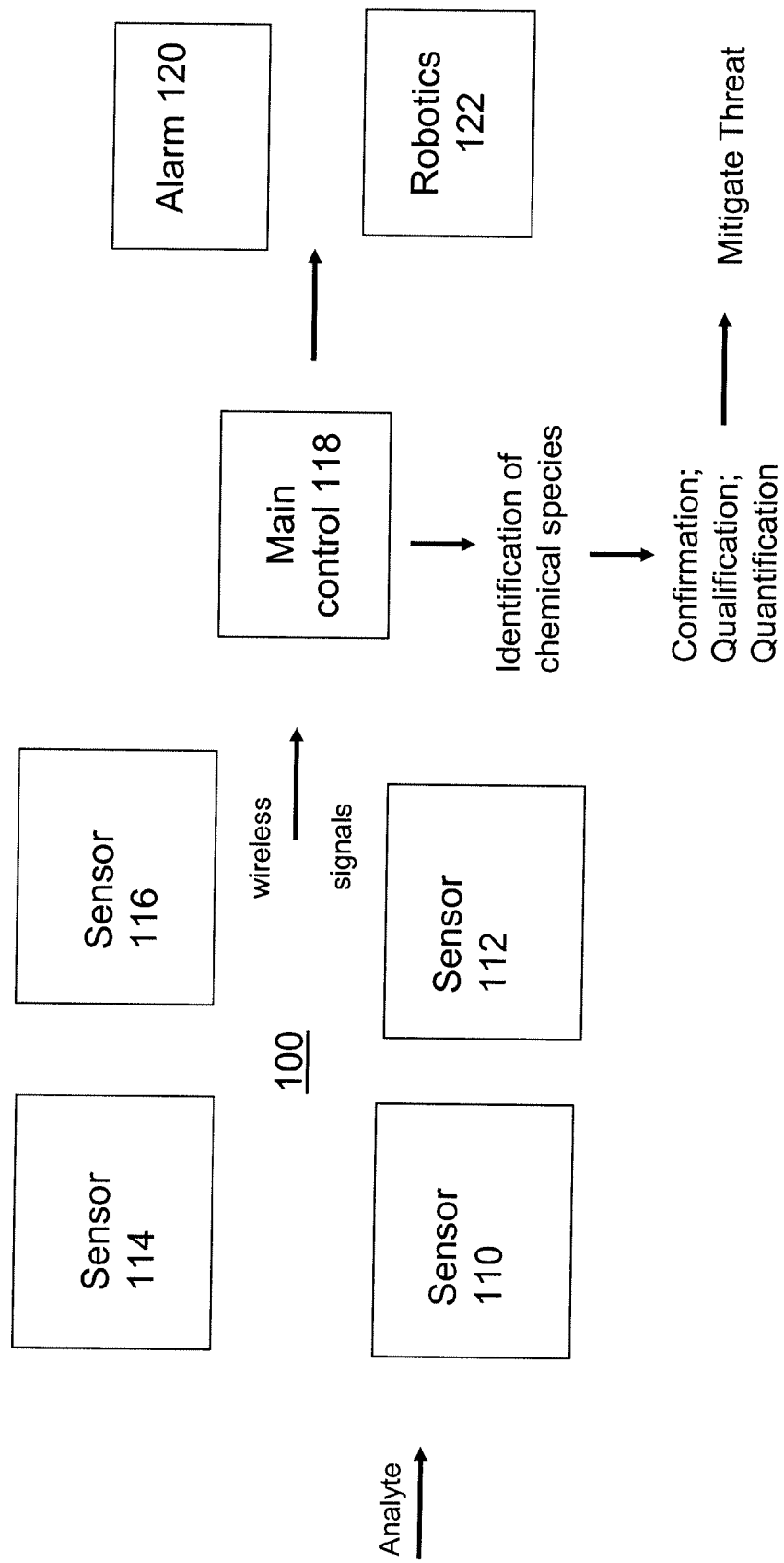

POLYMER NANOFIBER-BASED ELECTRONIC NOSE

CROSS REFERENCE TO RELATED APPLICATIONS

This application is related to U.S. application Ser. No. 10/819,916, filed on Apr. 8, 2004, entitled "Electrospinning of Polymer Nanofibers Using a Rotating Spray Head," the entire contents of which are incorporated herein by reference. This application is also related to U.S. application Ser. No. 10/819,942, filed on Apr. 8, 2004, entitled "Electrospray/electrospinning Apparatus and Method," the entire contents of which are incorporated herein by reference. This application is related to U.S. application Ser. No. 10/819,945, filed Apr. 8, 2004, entitled "Electrospinning in a Controlled Gaseous Environment," the entire contents of which are incorporated herein by reference. This application is related to U.S. application Ser. No. 11/559,282, filed on Nov. 13, 2006, entitled "Particle Filter System Incorporating Nanofibers," the entire contents of which are incorporated herein by reference. This application is related to U.S. application Ser. No. 11/670,774, filed on Feb. 2, 2007, entitled "A Thermal Preconcentrator for Collection of Chemical Species," the entire contents of which are incorporated herein by reference.

BACKGROUND OF THE INVENTION

1. Field of the Invention

The present invention relates to the field of artificial devices known as electronic noses for detecting chemical species.

2. Description of the Related Art

An electronic nose typically includes two components, an array of chemical sensors and a pattern-recognizer. The array "sniffs" vapors from a sample and provides a set of measurements; the pattern-recognizer compares the pattern of the measurements to stored patterns for known chemical species for identification of the sniffed vapor. Gas sensors tend to have very broad selectivity, and respond differently to different chemical species. This is a disadvantage in many applications, but in the electronic nose, it is utilized as an advantage. Although every sensor in an array may respond to a given chemical, these responses will usually be different. The pattern recognizer evaluates the responses and through predetermined, programmed, or learned patterns ascertains the chemical species affect on the gas sensor.

Recently, attention has been directed to chemically resistive microsensors, which are based on a polymer approach employing insulating polymers and conducting carbon black. In these microsensors, no individual sensor is highly selective toward an individual analyte or chemical species. Some works have shown that chemically sensitive resistors, formed from composites of carbon black with insulating organic polymers, are broadly responsive to a variety of odors. The classification and identification of organic vapors are made through the application of pattern recognition methods. So, the resistance change of sensors can be measured to obtain information about organic gases, as the sensors are exposed to gases.

Among the various electrodes, interdigitated microelectrode arrays have been used where particularly low detection limits are needed. These arrays show higher sensitivities than the conventional electrodes, such as circle electrodes in the area of the gas sensors. Yet, these sensors as reported in the literature have fairly slow response times (e.g., 10 s for detecting concentrations of 400 to 2000 ppm).

The electronic nose can match complex samples with subjective endpoints such as odor or flavor, determining for example when milk has turned sour or when a batch of coffee beans optimally roasted. For instance, the electronic nose can match a set of sensor responses to a calibration set produced by the human taste panel or olfactory panel routinely used in food science. The electronic nose can be used as a production tool to maintain quality over long periods of time.

Several commercial electronic-nose type sensors available are based on either metal oxide or intrinsically-conducting polymers (ICP) as the sensor element. The ones based on polymers include AromaScan™, Bloodhound™, Alpha-MOS™ and Zellweger™ analytics devices. Specifically, the AromaScan™ electronic nose, for example, has 32 different sensors in its array, each of which will in general exhibit a specific change in electrical resistance when exposed to air containing an odor. The selective interaction of odors with the sensors produces a pattern of resistance changes for each odor. If an odor is composed of many chemicals, the pattern will be the result of their combined interactions with all of the sensors in the array. It has also been found that the response of the array to varying concentrations of the same odor is non-linear.

In many of the commercial electronic nose sensors, polypyrrole (with different counter ions) electrodeposited as a film across a 10-50 micron gap on a gold interdigitated electrode is commonly used in these sensors. These commercial e-noses have been used to detect spoilage of food, growth of microorganisms, and have been used in medical applications.

Polymers that are typically insulators have been used in e-nose applications by using a conductive filler such as carbon black in the fibers. The filler level is controlled to be near the conduction percolation threshold to obtain high-gain sensors. When exposed to a volatile organic compound (VOC), the polymer swells and its resistance is changed. Spin casting of these polymers over an electrode surface is the conventional technique used to fabricate the commercial polymer-based electronic nose sensors. Multicomponent polymer arrays have been used in commercial devices to generate unique patterns or "fingerprints" associated with different VOCs. The Cyrano C 320™ e-nose system, for instance, uses 32 sensors.

Previously, commercial electronic nose devices used polymer films either electrodeposited or spin-coated on gold electrode assemblies. The response time for these composite assemblies (as given above) is a function determined by the diffusion kinetics of the vapors through polymer film, and is therefore long.

SUMMARY OF THE INVENTION

In one embodiment of the present invention, there is provided a chemical sensor including a plurality of nanofibers whose electrical impedance varies upon exposure to the chemical species, a substrate supporting and electrically isolating the fibers, and a set of electrodes connected to the plurality of fibers at spatially separated points to permit the electrical impedance of the plurality of fibers to be measured.

In another embodiment of the present invention, there is provided a system for sensing a chemical species including the above noted chemical sensor, an impedance measuring device coupled to the electrodes and configured to determine an electrical impedance of the plurality of fibers upon vapor analyte exposure, and an computer analyzer configured to identify the chemical species based on a change in the electrical impedance.

In another embodiment of the present invention, there is provided a method for sensing a chemical species which measures at least one change in an electrical impedance between spatially separated electrodes connected to a plurality of fibers upon exposure of the fibers to the chemical species, and identifies the chemical species based on the measured change in the electrical impedance.

It is to be understood that both the foregoing general description of the invention and the following detailed description are exemplary, but are not restrictive of the invention.

BRIEF DESCRIPTION OF THE DRAWINGS

A more complete appreciation of the present invention and many attendant advantages thereof will be readily obtained as the same becomes better understood by reference to the following detailed description when considered in connection with the accompanying drawings, wherein:

FIG. 6A is a flowchart depicting a method according to one embodiment of the present invention for making the chemical sensors of the present invention;

FIG. 9 is a schematic illustration showing an example of a network of chemical sensors according to one embodiment of the present invention.

DETAILED DESCRIPTION OF THE PREFERRED EMBODIMENTS

Figure 1:
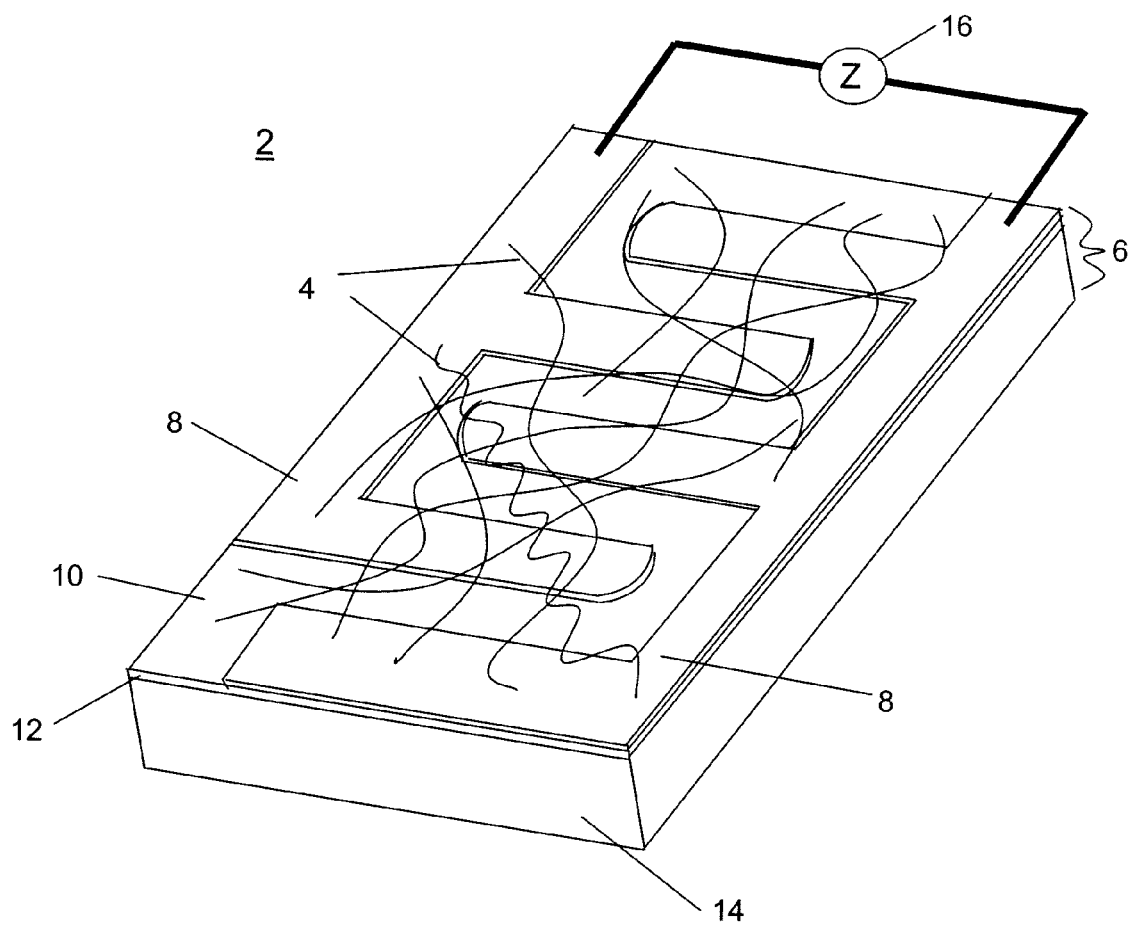
FIG. 1 is a schematic of a one embodiment of the invention showing a chemical sensor having a plurality of nanofibers as the sensing elements.

Referring now to the drawings, wherein like reference numerals designate like or corresponding parts throughout the several views, and more particularly to FIG. 1, FIG. 1 depicts chemical sensor 2 of the present invention in which fiber or nano-fiber based materials are used as the active sensing elements. As shown in FIG. 1, the sensing elements include a fiber mat 4 of fibers disposed on a substrate 6. In this embodiment depicted in FIG. 1, the mat of fibers has no preferred orientation. The use of nano-fibers for the fiber mat in one embodiment of the present invention affords high surface area and therefore faster reaction times. The fiber mat 4, in one embodiment of the present invention, includes carbon nanotubes and/or other conducting particles or nanoparticles such as for example gold particles.

As shown in FIG. 1, fibers of the fiber mat 4 are attached to electrodes 8 at longitudinal points of the fibers. The electrodes 8 as shown in FIG. 1 are disposed on an insulating surface 10. The insulating surface 10 in one embodiment of the present invention is an insulator 12 deposited on a silicon wafer 14 containing circuitry 16 to analyze the impedance of the fiber mat and more specifically the change in impedance of the mat of fibers. If an insulating substrate is used instead of wafer 14, insulator 12 may not be required. The circuitry 16 in one embodiment of the present invention includes a temperature sensor such as a platinum resistance element or a thermocouple so that any changes in temperature of the nanofibers are considered as part of the change in impedance, and thereby the change in impedance due to VOC absorption on the nanofibers can be distinguished from a temperature induced change in impedance.

In another embodiment of the present invention, the fibers can be immersed in an aqueous solution and traces of organic solvent present in the aqueous solution will swell the polymer nanofiber and lead to overall conductivity change of the sensing material. Thus, the chemical sensor of the present invention can be used in gaseous and liquid environments.

Figure 2:
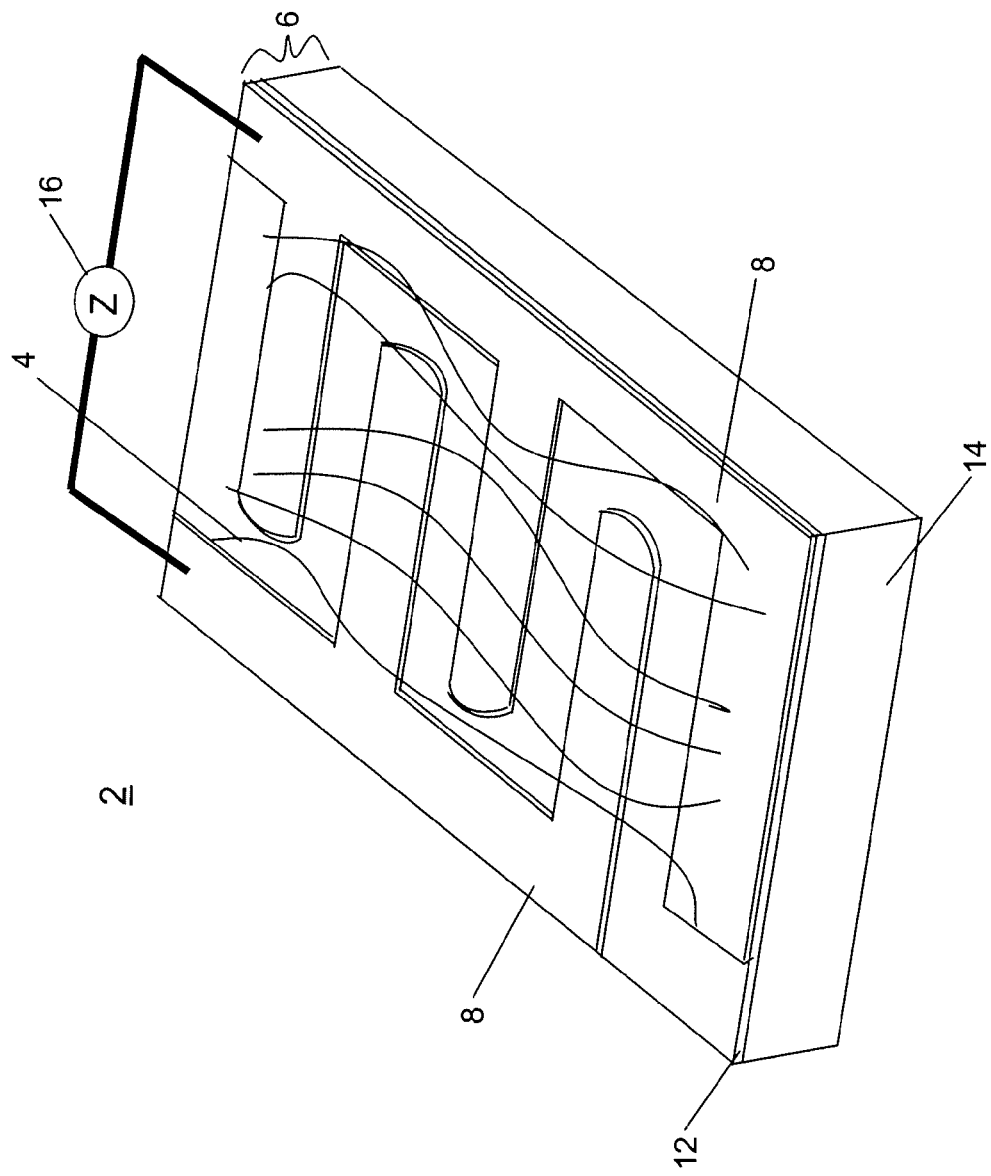
FIG. 2 is a schematic of a another embodiment of the invention showing a chemical sensor having a plurality of oriented nanofibers as the sensing elements.

As shown in FIG. 2, in one embodiment of the present invention, the fiber mat 4 can be preferentially oriented (formed for example by methods described below). In this embodiment, the change in impedance is more pronounced than in the configuration shown in FIG. 1 when the fiber mat 4 does not have a preferential alignment. Aligned fibers can help increase the reproducibility of the sensor response. Experience has shown that a higher degree of alignment produces more reproducible sensor responses. As shown in FIGS. 1 and 2, in one embodiment of the present invention, an interdigitated electrode 8 is used. One suitable interdigitated electrode has 15 µm electrode width and 15 µm electrode spacing. Other spacings in the range of 1 µm to 50 µm are also suitable for the present invention.

Figure 3A:
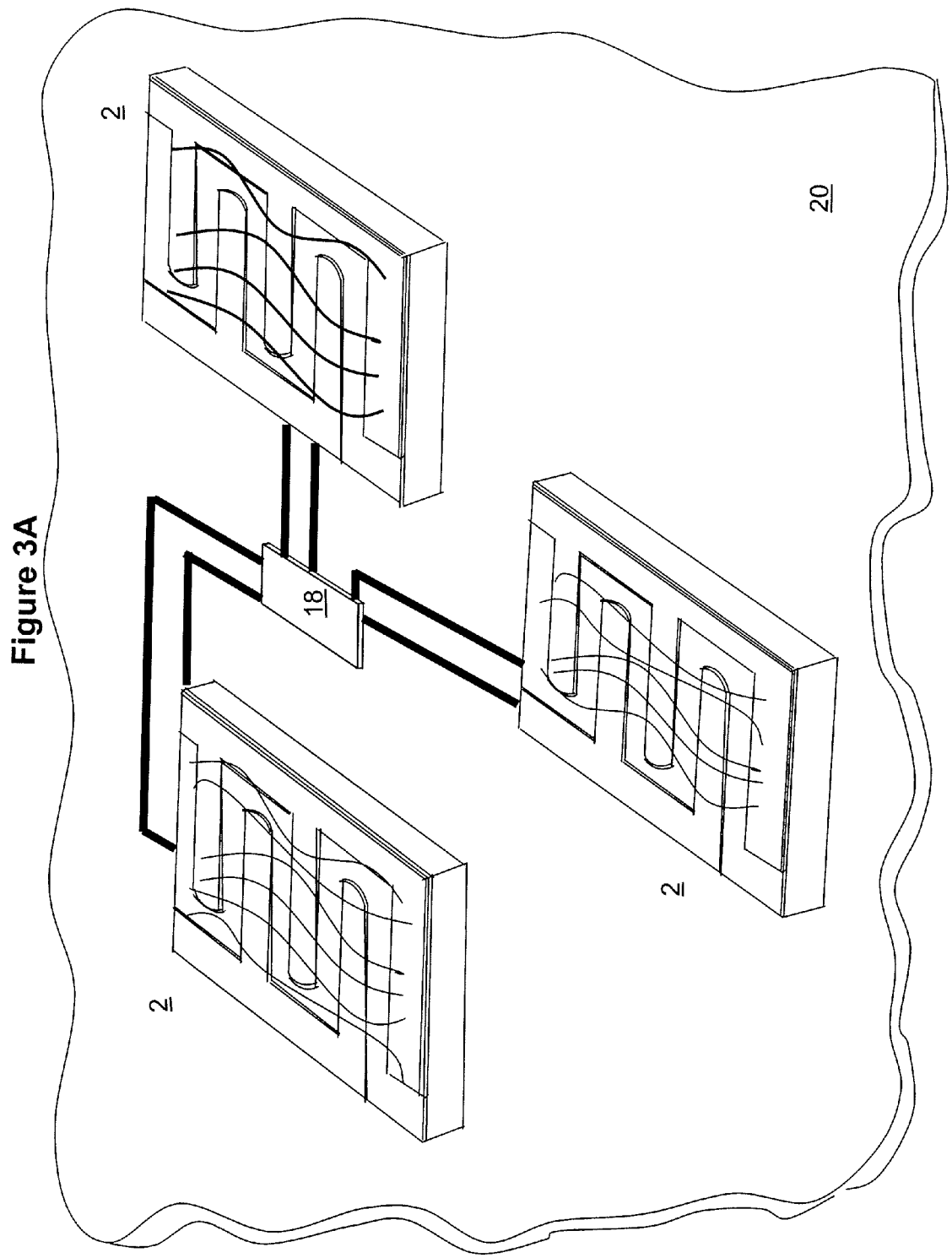
FIG. 3A is a schematic of another embodiment of the invention showing a chemical sensor system utilizing the sensing elements in FIG. 2, integrated onto a silicon device chip, and coupled to an analyzer.

As shown in FIG. 3A, in one embodiment of the present invention, the sensors 2 can be coupled to an analyzer 18, that determines a change of impedance of the nanofibers based on adsorption of a chemical species. The analyzer 18 can be a general purpose computer as described later in relation to FIG. 8. The analyzer 18 is programmed with instructions by which the chemical species inducing the impedance change can be deduced. Further, as shown in FIG. 3A, multiple sensors 2 can be used where the fibers or nanofibers on each sensor 2 preferentially react to a particular chemical species. While shown in FIG. 3A as integrated onto a silicon wafer die 20, the sensors and analyzer 18 can be integrated onto a circuit board.

The adsorbed chemical species swell the polymer composing the fibers or nanofibers which induces a change in the impedance of the composite nanofiber. During a sensing process of the present invention, a set of data on for example resistance variations for the entire array of sensing materials will be obtained and analyzed by a pattern recognition engine.

The extracted feature for each individual chemical species will be compared to a database obtained from the massive screening and data collection during validation of the chemical sensor system.

Figure 3B:
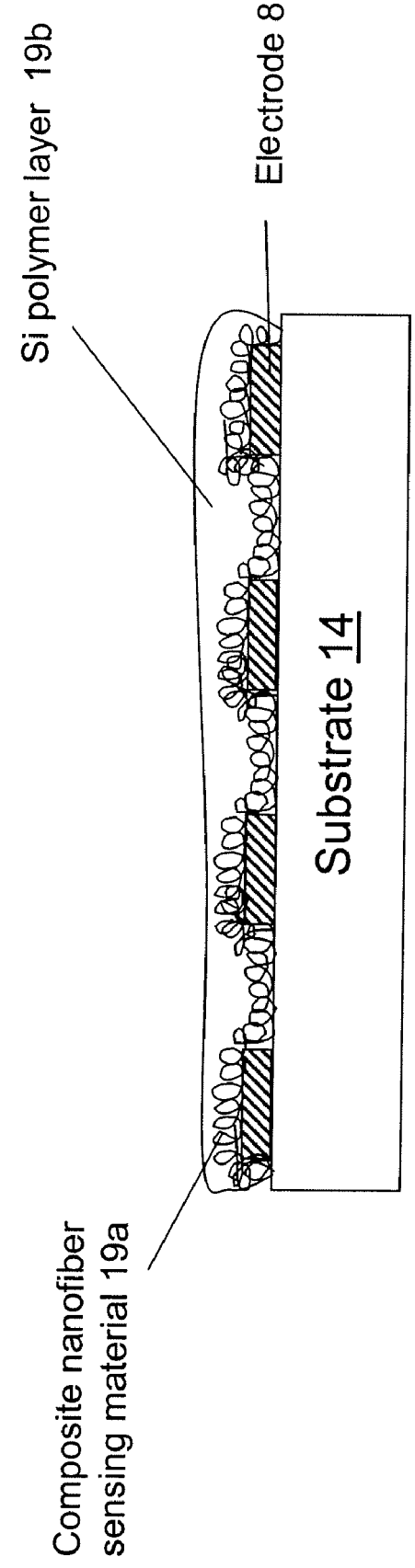
FIG. 3B is a schematic illustration showing a sensor device according to one embodiment of the present invention enveloped in a thin film of silicone rubber or other polymer that sorbs and concentrates VOCs from air.

In one embodiment of the present invention, as shown in FIG. 3B, a sensor device 2 is formed by a sensing material 19a enveloped in a thin film 19b of silicone rubber or other polymer that sorbs and concentrates VOCs from air. The sensing material such as for example the above-described fiber mats is deposited onto interdigitated microelectrode and the inter-digitated electrode is connected to a resistance measuring device (not shown here for the sake of simplicity) for data-logging such as for example the analyzer 18 of FIG. 3A. The data in one embodiment of the present invention is transferred by a computer interface. The data is then compared to existing saved databases for identification of the VOC or, if unknown at the time, saved to a sensor response database for future reference.

In the embodiment shown in FIG. 3, electrodes 8 contact the side of the fiber mat toward the substrate. The thickness of the overcoat layer is between 200 nm-2 µm. A cross-linked polydimethylsiloxane (PDMS) film is suitable for this purpose. As shown in FIG. 3B, the fiber mat 4 is encased between the film 19 and the substrate 14. A high partition coefficient for VOCs (as explained below) will ensure a higher concentration of the ambient VOC in PDMS as opposed to in air. The availability of a concentrated source of the VOC in the silicone matrix, next to the nanofiber-based sensor improves the sensitivity and the detection limit of the sensor device of the present invention. When two phases (in this case ambient air and the silicone polymer) are in contact with each other, at equilibrium a given VOC in air distributes into the two phases. The ratio of their concentrations in the two phases is the partition coefficient. The partition coefficient varies with the nature of the VOC and can assume a variety of values. In one embodiment of the present invention, the concentration of VOC in the vicinity of the silicone encapsulated electrode is increased, as the partition coefficient becomes >>1.

In one embodiment of the present invention, (n or p doped) intrinsically conducting polymers might also be used. In one embodiment of the present invention, the nanotubes are used as a reinforcing filler in the polymers to improve mechanical integrity. Other conducting materials can also be used as dopants in the polymer nanofiber, such as particles of metal and carbon.

In one embodiment of the present invention, the polymers are conductive polymers that do not necessarily have to be doped. Such polymers include for example polyaniline, polypyrrole, and polythiophene. These polymers typically have a resistivity of $10^{-5}$ Ω-cm or less.

Figure 3C:
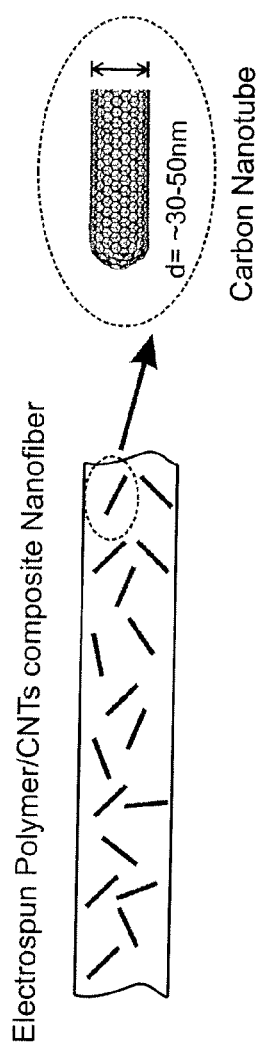
FIG. 3C is a schematic diagram showing the inclusion of carbon nanotubes in a sensor fiber of the present invention.

In one embodiment of the present invention, carbon nanotubes (SWCN) or multi-wall carbon nanotubes (MWCN) are used to affect the conductivity of the fibers. For example, the use of 1-30 weight percent of the single wall carbon nanotubes (SWCN) or the multi-wall carbon nanotubes (MWCN) changes the electrical resistivity of conventional polymers such as polycarbonates, acrylic polymers or polysulfone. Indeed, concentrations of SWCN or MWCN within 10% of the conduction percolation threshold are suitable for the present invention. Carbon nanotubes can be used at levels that are at or considerably above or below this threshold. FIG. 3C is a schematic diagram showing the inclusion of carbon nanotubes in a sensor fiber of the present invention. From this figure, it can be seen that expansion of the fiber polymer would increase the separation distance between the carbon nanotubes and increase the impedance of the fiber to electrical conduction.

A suitable electrode in one embodiment of the present invention is an interdigitated electrode 8 having for example a gap of 50 microns. Gold is a suitable electrode material, but other electrodes such as Ag, Cu, Al, W, Ta, and Tn can be used. Any conducting metal can be used the electrode materials.

Additionally, in one embodiment of the present invention the electrodes can be formed by a printing process. Instead of the preformed inter-digitated gold electrodes discussed above, printed electrodes are used. In this embodiment, a set of electrodes of a suitable geometry are printed using a chemical printer or a modified inkjet printer loaded with a conducting ink. The electrodes can be printed on top of (or below) a composite fiber or nanofiber (polymer+carbon nanotubes) mat that is generated on top of a gas permeable membrane, a glass or non-conducting material. The geometry may or may not be interdigitated and the distance between electrodes can be varied according to the present invention. This approach permits low-cost fabrication of sensors and their application on textile or other surfaces. Other printing methods (such as screen printing) can be used according to the present invention.

Figure 3D:
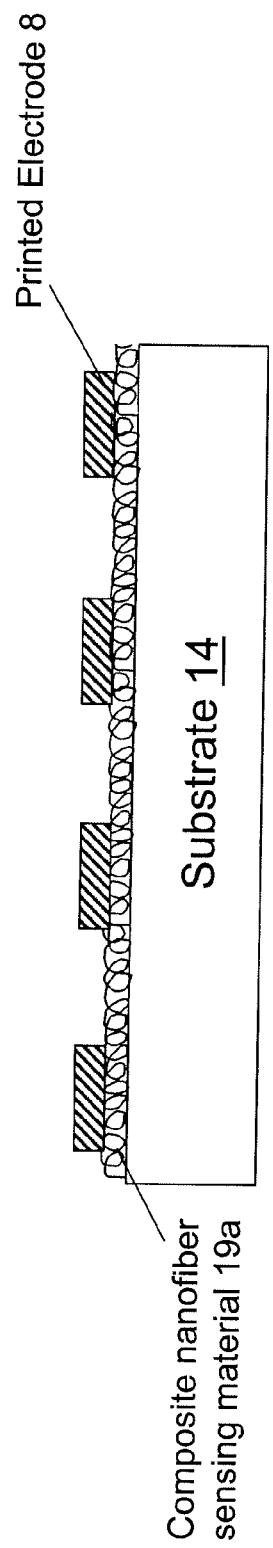
FIG. 3D is a schematic illustration showing according to one embodiment of the present invention a chemical sensor having printed electrodes on the top of the electrospun nanofiber sensing material.

FIG. 3D is a schematic illustration showing, according to one embodiment of the present invention, a chemical sensor 2 having printed electrodes 8. In this embodiment of the present invention, the printed electrodes 8 are formed on the fiber mat 4 at designated positions above for example a glass or quartz substrate 12.

Alternatively, in one embodiment of the present invention, the electrodes are formed on top of a mat of pre-spun fibers. Besides printing, sputter coating could be used to deposit electrode materials through a shadow mask to produce a desired electrode pattern on the fiber mat.

Whether by ink jet printing, screen printing, or sputtering or other known processes for electrode patterning, medium such as for example fabric, paper, plastic, ceramic, gas permeable membrane or other material may have electrodes placed on one or both surfaces of the medium and in turn placed in contact with the fiber mat.

In one embodiment of the present invention, nanofiber sensing elements are directly electrospun from sonicated solutions of the carbon nanotubes (CNT) and polymer material onto an appropriate electrode system maintained at a ground potential or at a high potential of opposite polarity from the electrospinning units.

A polymer solution in dimethylformamide. (DMF) containing 20 percent (w/w) of polymethyl-methacrylate (PMMA) polymer and 10% (w/w on polymer) of single wall carbon nanotubes (SWCNT) sonicated for a period of 8 hours is, according to the present invention, a suitable electrospinning solution by which to electrospin the nanofibers. Such a solution may be electrospun for example in the apparatus described in U.S. application Ser. No. 10/819,945, filed Apr. 8, 2004, entitled "Electrospinning in a Controlled Gaseous Environment," the entire contents of which are incorporated herein by reference.

Figure 4:
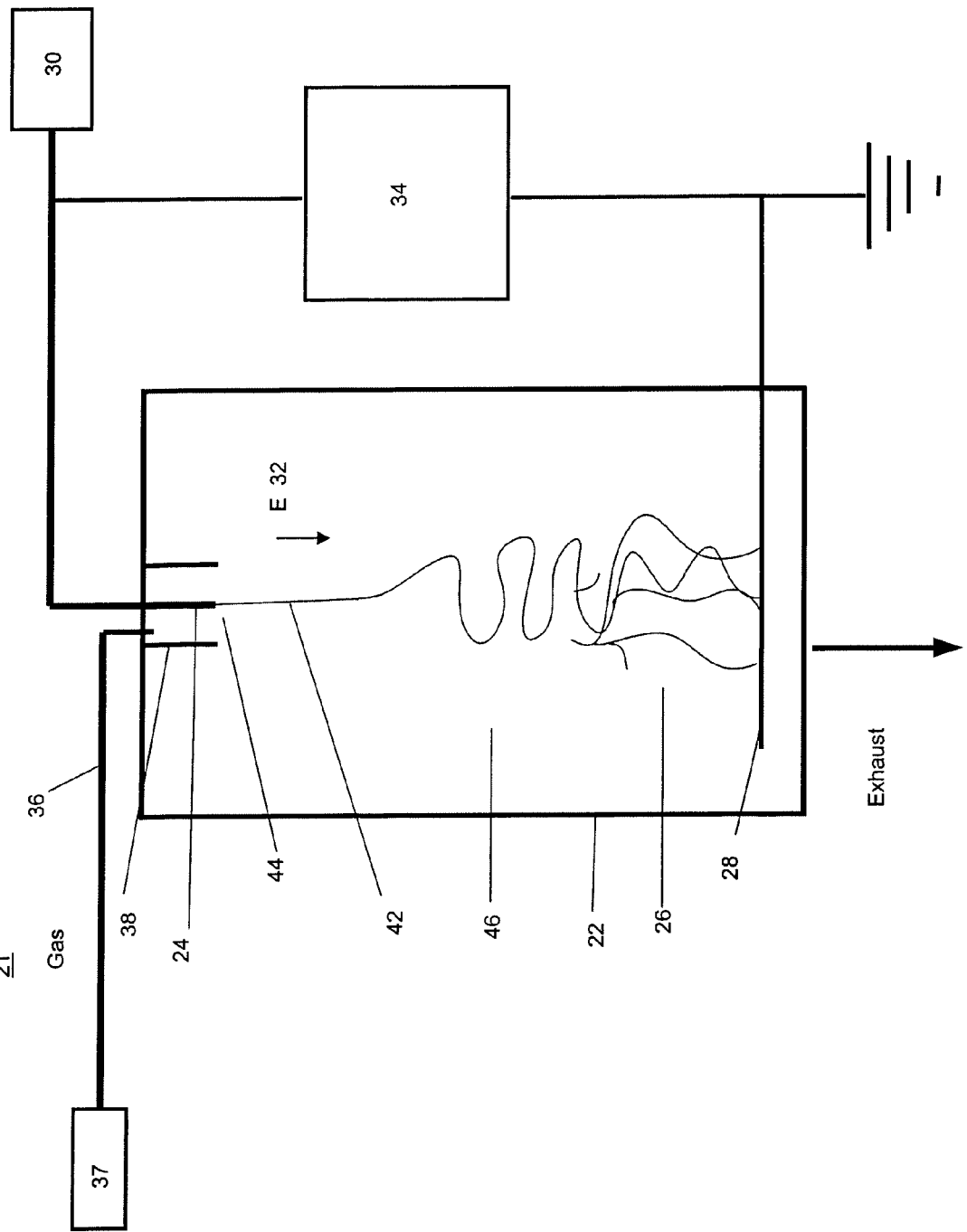
FIG. 4 is a schematic illustration depicting an electrospinning apparatus suitable for deposition of fibers and nanofibers of the present invention.

FIG. 4 is a schematic illustration depicting an electrospinning apparatus suitable for deposition of nanofibers of the present invention. FIG. 4 is a schematic illustration of an electrospinning apparatus 21 according to one embodiment the present invention in which a chamber 22 surrounds an electrospinning electrospinning element 24. As such, the electrospinning element 24 is configured to electrospin a substance from which fibers are composed to form fibers 26. The electrospinning apparatus 21 includes a collector 28 disposed from the electrospinning element 24 and configured to collect the fibers.

The electrospinning element 24 communicates with a reservoir supply 30 containing the electrospin medium such as for example the above-noted polymer solution. The electrospin medium of the present invention includes polymer solutions and/or melts known in the art for the extrusion of fibers including extrusions of nanofiber materials. Indeed, polymers and solvents suitable for the present invention include for example polystyrene in dimethylformamide or toluene, polycaprolactone in dimethylformamide/methylene chloride mixture (20/80 w/w), poly(ethyleneoxide) in distilled water, poly(acrylic acid) in distilled water, poly(methyl methacrylate) PMMA in acetone, cellulose acetate in acetone, polyacrylonitrile in dimethylformamide, polylactide in dichloromethane or dimethylformamide, and poly(vinylalcohol) in distilled water. Thus, in general, suitable solvents for the present invention include both organic, inorganic solvents or aqueous solution in which polymers can be dissolved.

A high voltage source 34 is provided to maintain the electrospinning element 24 at a high voltage. The collector 28 is placed preferably 1 to 100 cm away from the tip of the electrospinning element 24. The collector 28 can be a plate or a screen. Typically, an electric field strength between 2,000 and 400,000 V/m is established by the high voltage source 34. The high voltage source 34 is preferably a DC source, such as for example Bertan Model 105-20R (Bertan, Valhalla, N.Y.) or for example Gamma High Voltage Research Model ES30P (Gamma High Voltage Research Inc., Ormond Beach, Fla.). Typically, the collector 28 is grounded, and the fibers 26 produced by electrospinning from the electrospinning elements 24 are directed by the electric field 32 toward the collector 28.

With reference to FIG. 4, the electric field 32 pulls the substance from which the fiber is to be composed as a filament or liquid jet 42 of fluid from the tip of the electrospinning element 24. A supply of the substance to each electrospinning element 24 is preferably balanced with the electric field strength responsible for extracting the substance from which the fibers are to be composed so that a droplet shape exiting the electrospinning element 24 is maintained constant.

As illustrative of the electrospinning process of the present invention, the following non-limiting example is given to illustrate selection of the polymer, solvent, a gap distance between a tip of the electrospinning element and the collection surface, solvent pump rate, and addition of electronegative gases:

a polystyrene solution of a molecular weight of 350 kg/mol,
a solvent of dimethylformamide DMF,
an electrospinning element tip diameter of 1000 μm,
an Al plate collector,
0.5 ml/hr pump rate providing the polymer solution,
an electronegative gas flow of $CO_2$ at 8 Lpm,
an electric field strength of 2 KV/cm, and a gap distance between the tip of the electrospinning element and the collector of 17.5 cm.

Furthermore, as illustrated above in FIG. 2, in one embodiment of the present invention oriented nanofibers are produced. To obtain aligned nanofibers, both electrodes might be grounded or held at a potential of opposite polarity (relatively to the spinhead). Further, techniques as described in U.S. application Ser. No. 10/819,916, filed on Apr. 8, 2004, entitled "Electrospinning of Polymer Nanofibers Using a Rotating Spray Head," the entire contents of which are incorporated herein by reference, can be used in the present invention to produce oriented fibers.

Figure 5A:
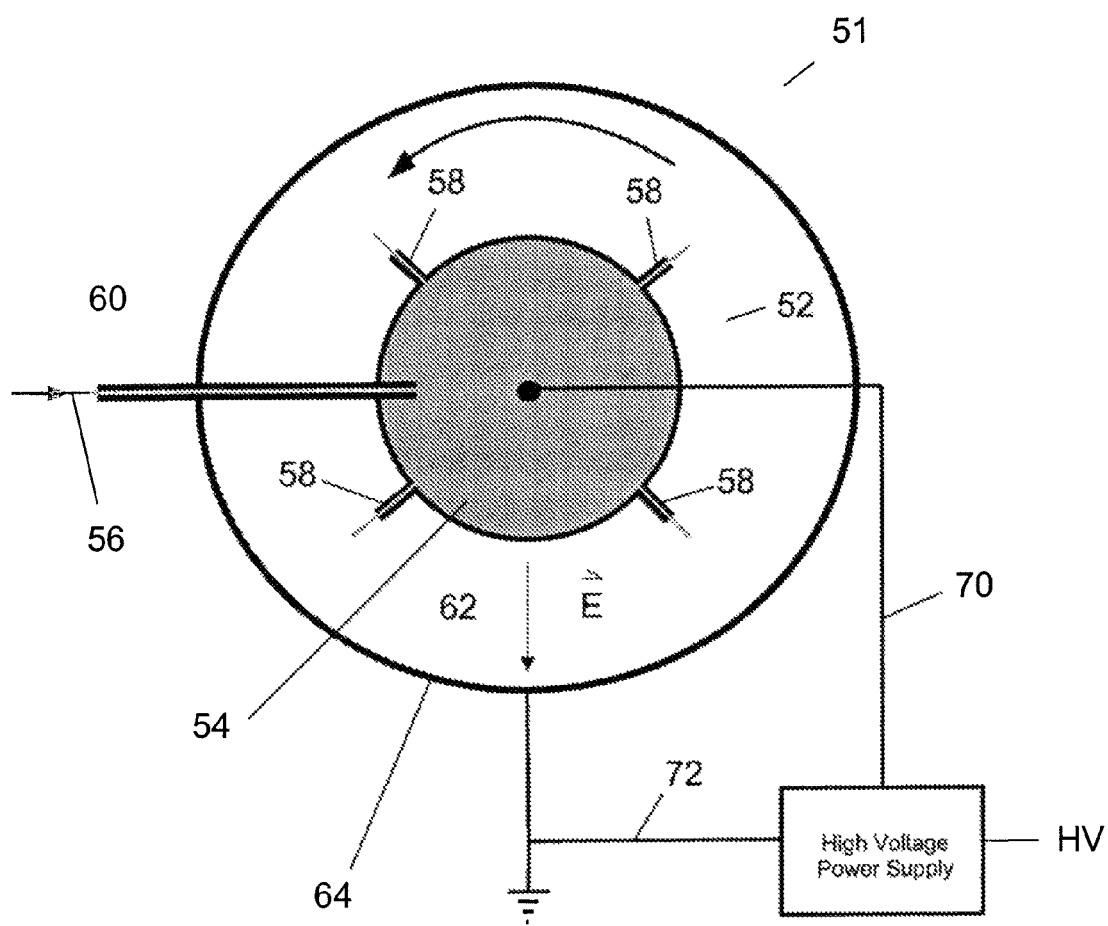
FIG. 5A is a schematic illustration showing a top view of an electrospinning apparatus 21 of one embodiment of the present invention for electrospinning oriented conducting fibers and nano-fibers.
Figure 5B:
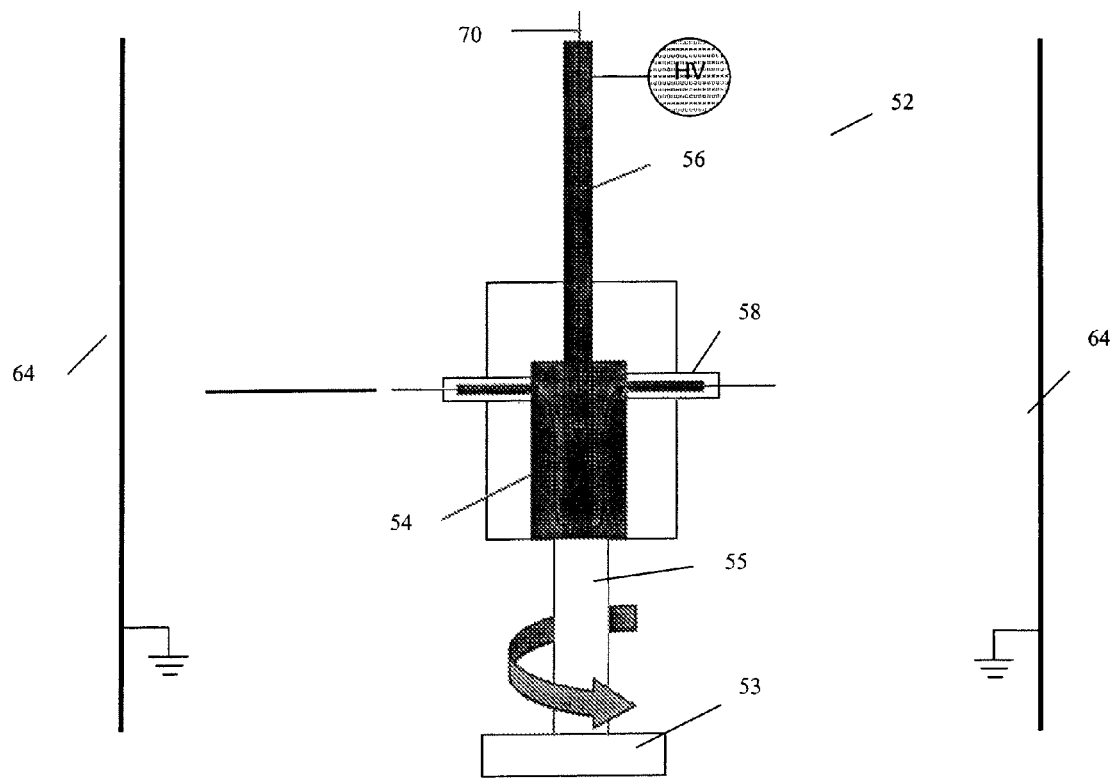
FIG. 5B is a schematic illustration showing a side view of an electrospinning apparatus in FIG. 5B.

FIG. 5A is a schematic illustration showing a top view of an electrospinning apparatus 51 for electrospinning oriented conducting nanofibers. FIG. 5A depicts a rotatable spray head 52 including a reservoir 54 holding a substance from which the fibers are to be extruded. FIG. 5B shows a side view of the electrospinning apparatus 51. In FIG. 5B, the electrospray medium is shown illustratively being feed to the reservoir 54 along an axial direction of the electrospinning apparatus 51. The electrospray medium 56 is electrospun from a plurality of electrospinning elements 58. The rotatable spray head 52 is preferably rotated about its center, and the spray of the electrospray medium 56 occurs radially from the electrospinning elements 58 placed on the periphery of the rotatable spray head 52. The rotatable spray head 52 is preferably a cylindrical structure, but other structures such as for example polygonal structures are suitable. The rotatable spray head 52 includes a passage 60 for supplying the electrospray medium 56 to the reservoir 54.

An electric potential applied to the rotatable spray head 52 establishes an electric field 62 as shown in FIG. 5A which extends to a collector 64 constituting an opposite electrode. The geometrical arrangement of the rotatable spray head 52 and the collector 64 configures the electric field strength and distribution. An electric field strength of about 3 kV/cm in the present invention is preferred. In the present invention, the spray head 52 constitutes an electrifiable chamber (i.e., a chamber upon which an electric potential can be established). The electrospray medium 56 upon extraction from a tip of the plural electrospinning elements 58 is guided along a direction of the electric field 52 toward the collector 64, but is deflected according to the centrifugal forces on the electrospun fibers.

The rotatable spray head 52, shown for example in FIG. 5A, can be a cylindrical vessel. On spinning, the electrospray medium 56 being a viscous solution is forced into the electrospinning elements 58. The electric field 62 existing about the rotatable spray head 52 then extracts the electrospray medium 56 from the reservoir 54 to a tip end of the electrospinning elements 58. The extracted medium 56 dries in the ambient about the rotatable spray head 52 to form fibers.

Upon extrusion from the rotatable spray head 52, the electrospun fibers collect on the collector 64. The collected fibers are deposited on the surface of the collector 64 with a degree of orientation dependent on the speed of rotation, the electric potential of the rotatable spray head 52, and the viscosity of the solution. According to the present invention, the fiber characteristics as well as the orientation can be controlled by the centrifugal forces generated by the spinning of the rotatable spray head 22 to be discussed below.

The electric field 62 is produced between the rotatable spray head 52 and the collector by applying a high voltage power source HV, as shown in FIG. 5A. The high voltage power source HV can be commercial power source, such as for example Bertan Model 105-20R (Bertan, Valhalla, N.Y.) or for example Gamma High Voltage Research Model ES30P (Gamma High Voltage Research Inc., Ormond Beach, Fla.). Typically, an electric field strength between 2,000 and 400,000 V/m is established by the high voltage source.

The collector 64 can be grounded, and the fibers produced by electrospinning are directed by the electric field 62 toward the collector 64. The electrospun fibers are deposited on the collector 64, accumulate thereon, and are subsequently removed. A rotating mechanism (not shown) rotates the rotatable spray head 62 at a preset angular speed. An angular rotation speed of 500-10,000 rpm is preferred.

Electrospinning of polymer solutions containing carbon nanotubes (single or multi walled) is similar to the electrospinning polymers without the nanotubes. However, care must be taken to sonicate the carbon nanotubes in solvent prior to mixing with the polymer to ensure adequate dispersion. Adequate dispersion results in uniform conductivity as well as the ability to reach a percolation threshold at low concentrations of the conducting filler material. Normally, a sonication time greater than 24 hours is sufficient to obtain a uniform carbon nanotube suspension in the solution. Normally <5% of carbon nanotubes will make the percolation threshold; however, this value of carbon nanotube concentration depends on the length of the carbon nanotubes. Accordingly, concentrations of carbon nanotubes suitable for the present invention in those embodiments at the percolation threshold range from 2% to 10%.

FIG. 6A is a schematic depicting a flowchart according to a method of the present invention. As depicted in FIG. 6A, one method of the present invention includes in step 602 providing a substrate for support of nanofibers. The method includes in step 604 depositing electrodes on the substrate. The method includes in step 606 depositing on the substrate and contacting the electrodes a plurality of conductive gas-absorbing nanofibers whose electrical resistance varies upon exposure to a chemical compound.

In step 606, the method preferably electrospins the substance in an electric field strength of 2,000-400,000 V/m. The nanofibers produced by the present invention include, but are not limited to, acrylonitrile/butadiene copolymer, cellulose, cellulose acetate, chitosan, collagen, DNA, fibrinogen, fibronectin, nylon, poly(acrylic acid), poly(chloro styrene), poly(dimethyl siloxane), poly(ether imide), poly(ether sulfone), poly(ethyl acrylate), poly(ethyl vinyl acetate), poly (ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly(vinylpyrrolidone), proteins, SEBS copolymer, silk, and styrene/isoprene copolymer.

Additionally, polymer blends can also be produced as long as the two or more polymers are soluble in a common solvent. A few examples would be: poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly (ethylene oxide), protein blend-polyethyleneoxide, polylactide-blend-polyvinylpyrrolidone, polystyrene-blend-polyester, polyester-blend-poly(hyroxyethyl methacrylate), poly(ethylene oxide)-blend poly(methyl methacrylate), poly (hydroxystyrene)-blend-poly(ethylene oxide)).

The fibers deposited in the one embodiment of the present invention may range from 50 nm to several microns in diameter and may contain amounts of carbon nanotubes or other conductive filler varying from a fraction of a percent to 20 or 30 percent by weight. Besides, carbon nanotubes, dopants such as metallic particles can be used to permit the deposited nanofibers to be electrically conductive.

Further refinements of the electrospining process are described in U.S. application Ser. No. 11/559,282, filed on Nov. 13, 2006, entitled "Particle Filter System Incorporating Nanofibers," previously incorporated herein by reference. The practices described there can be used in the present invention to produce small diameter nanofibers whose large surface to volume ratio will enhance the sorption of chemical species in the various chemical sensors of the present invention.

In one embodiment of the present invention, stainless steel extrusion tips having internal diameters (ID) from 0.15 to 0.58 mm are used. In another refinement, polytetrafluroethane (i.e., Teflon) capillary tubes with ID from 0.07-0.30 mm are used. Both types of orifices can produce submicron fibers. For both orifices, low flow rates coupled with high voltage drops typically resulted in the smallest fiber diameters (e.g, <200 nm). In both cases, the voltage was 22 kV to 30 kV for a 17.8-25.4 cm gap (i.e., the distance between tip 16 and electrode 20). In one embodiment of the present invention, the voltage per gap is a parameter providing pulling strength for the electrospinning. The gap in part determines travel time of the electrospun fiber to the collector, and thus determines stretching and solvent evaporation times. In one embodiment of the present invention, different $CO_2$ purge flow rates around needle 18 (i.e., as a gas jacket flow around and over the tip 16 in the fiber pull direction) for the different spinning orifices are utilized to improve the electrospun fibers.

When stainless steel needles were used, higher gas flow rates of $CO_2$ (e.g., increasing from 81 pm to 131 pm) typically resulted in improved fibers with smaller diameters. Reductions of 30 to 100 nm in AFD were observed, permitting (in most cases) fibers with AFD less than 200 nm to be achieved by these methods of the present invention.

In contrast, when Teflon capillary tubes were used, the fiber quality was usually degraded with increasing $CO_2$ flow rate from 81 pm to 131 pm. The number of beads and other fiber defects increased. For Teflon capillary tube, a flow rate of about 81 pm is suitable for small (less than 200 nm) diameter fibers, whereas a higher flow rate is suitable for stainless steel capillary tubes. The values for electronegative gas flow rates (in this case $CO_2$) given here are only examples, other gas flow rates may be used given the combination of electrospinning orifice, polymer formulation, and electrospinning conditions used in order to obtain small diameter nanofibers.

In one embodiment of the present invention, the relative humidity RH of the electrospinning chamber also effects fiber morphology. In one example, using 21 wt % PSu in DMAC, a high RH>65%, resulted in fibers that had very few defects and smooth surfaces but larger diameters, as compared to electrospun fibers produces at RH>65%. Low RH<13%, resulted in smaller fibers but having more defects (e.g., deviations from smooth round fibers). Modestly low RH, 40% to 22%, typically produced a small fiber size with fewer defects.

A variety of mechanisms to control the chamber RH are available, according to various embodiments of the present invention, from placing materials that absorb (e.g. calcium sulfate) or emit water moisture (e.g., hydrogels) in the electrospinning chamber, operating a small humidifier in the chamber, or other ways of introducing moisture into the electrospinning chamber. For example, suitable results were obtained by bubbling $CO_2$ through deionized water and then introducing the humidified gas into the chamber. Two gas streams (one humidified and one dry) can be used to obtain a desired RH for the chamber and/or for the gas jacket flowing over the electrospinning orifice.

Thus, in one example of the present invention, a combination of a Teflon capillary tube, an 81 Lpm $CO_2$ purge rate, under a RH of 30%, using PSu in DMAC produced nanofibers with an AFD of less than 100 nm. While a combination of a stainless steel capillary tube, a 131 pm $CO_2$ purge rate, under a RH of 30%, using PSu in DMAC produced nanofibers with an AFD of less than 100 nm.

In another example of the present invention, nanofibers were electrospun with a solution of 21 wt % PSu in N,N-dimethylacetamide (DMAC), with the solution containing 0.2 wt. % of the surfactant tetra butyl ammonium chloride (TBAC). The surfactant lowers the surface tension and raises the ionic conductivity and dielectric constant of the solution. The polymer solution was spun from a 30 G (ID 0.154 mm) stainless steel needle with a flow rate of 0.05 ml/hr, a gap of 25 cm between the needle and target, an applied potential of 29.5 kV DC, a $CO_2$ gas jacket flow rate of 6.51 pm, and an RH in the range of 22 to 38%. Inspection by SEM indicated an average fiber diameter (AFD) of 82±35 nm with the smallest observed fibers being in the 30 to 40 nm range.

In another example, polycarbonate PC can be spun from a 15 wt % solution of polymer in a 50/50 solution of tetrahydrofuran (THF) and N,N-dimethyl formamide (DMF) with 0.06 wt % TBAC. A 30 gauge stainless steel needle, a polymer solution flow rate of 0.5 ml/hr, and a $CO_2$ flow rate of 81 pm were used with a gap of 25.4 cm and applied potential of 25 kV to obtain sub 200 nm fibers. Inspection by SEM indicated an AFD of 150±31 nm with the smallest fibers being around 100 nm.

Work in development of the present invention has shown that direct electrospinning of nanofibers on gold electrodes may not always result in adequate electrical contact between the nanofibers and metal to allow the sensor to function satisfactorily. To address this shortcoming, in one embodiment of the present invention, a spincoat of a bonding polymer such as propylene glycol monomethyl ether (PGME) is applied prior to electrospinning the fibers or nano-fibers to promote electrical contact to an underlying conductive substrate such as for example a gold or gold plated substrate. Other polymers that have appropriate functional groups capable of non-bonded interaction with the fiber mat might also be used in place of PGME.

In another embodiment of the present invention, electrical contact between an electrode and a conductive filler (or additive) in the nanofiber such as carbon nanotubes is enhanced by treating the nanofiber/electrode assembly to promote local enhancement in the conductivity between the conductive filler and the electrode. For example, in one illustration, the electrodes are heated to locally deform the nanofibers, thereby promoting better electrical contact between nanofibers and electrode.

Alternatively, the electrical connection can be improved (as detailed before) by printing electrode with a conductive ink including a solvent for the fiber as one of its solvent components.

Once the fibers or nanofibers have been electrospun, the chemical sensor is thoroughly dried to remove residual spinning solvents and is connected via the electrode terminals to a recording meter included for example in the circuitry 16 or in the analyzer 18 to read the impedance across the electrodes. For example, the change can be reported as dimensionless resistance change ($\Delta R/R$). This quantity changes with the amount of VOC in the immediate environment of the sensor. This technology relies on pattern recognition applied to empirical sensor array resistance data to distinguish one VOC from another. As in conventional E-nose systems, each VOC of interest will essentially have a 'fingerprint' in terms of its effect on the individual sensor elements.

Figure 6B:
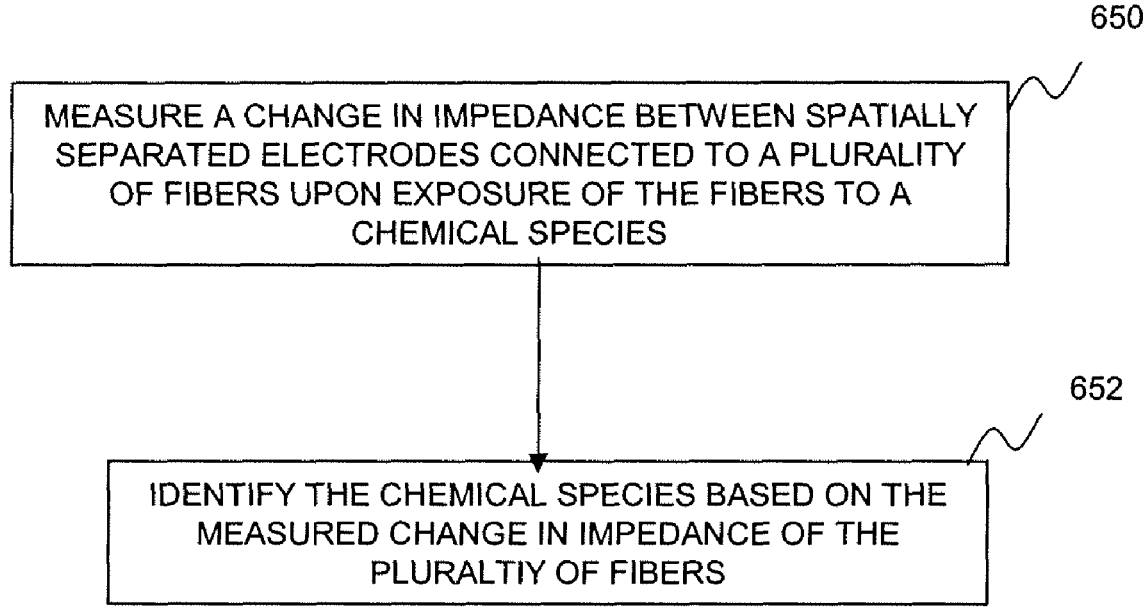
FIG. 6B is a flowchart depicting a method according to one embodiment of the present invention for sensing a chemical species.

FIG. 6B is a schematic depicting a flowchart according to a method of the present invention for identifying a chemical species (e.g., an airborne chemical species). At 650, a change in electrical impedance (e.g., capacitance, inductance, or resistance) between spatially separated electrodes connected to a plurality of fibers upon exposure of the fibers to the chemical species. At 652, the chemical species is identified based on the change in the electrical impedance of the plurality of fibers.

At 650, the change in electrical impedance can be measured for a plurality of nanofibers whose average fiber diameter is less than 500 nm or less than 100 nm. The change in electrical impedance can be measured for a plurality of conductive fibers. The conductive fibers can have a non-conducting medium and a conducting medium such that a density of the conducting medium in the fibers permits electrical conduction by percolation of charge carriers between regions of the conducting medium.

At 652, the chemical species can be identified by comparing the measured change to a library of changes for known concentrations of predetermined chemical species or by comparing measured changes for a plurality of different fibers to a library of changes for known concentrations of different predetermined chemical species.

Figure 7A:
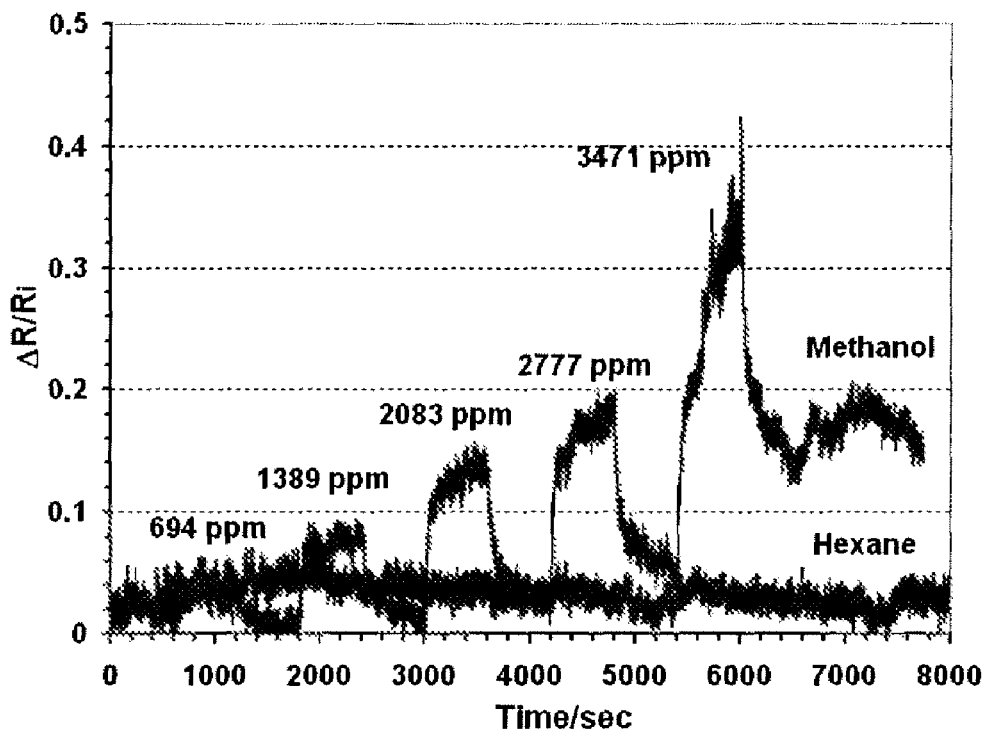
FIGS. 7A and 7B are graphs showing a typical response of the chemical sensor of the present invention.
Figure 7B:
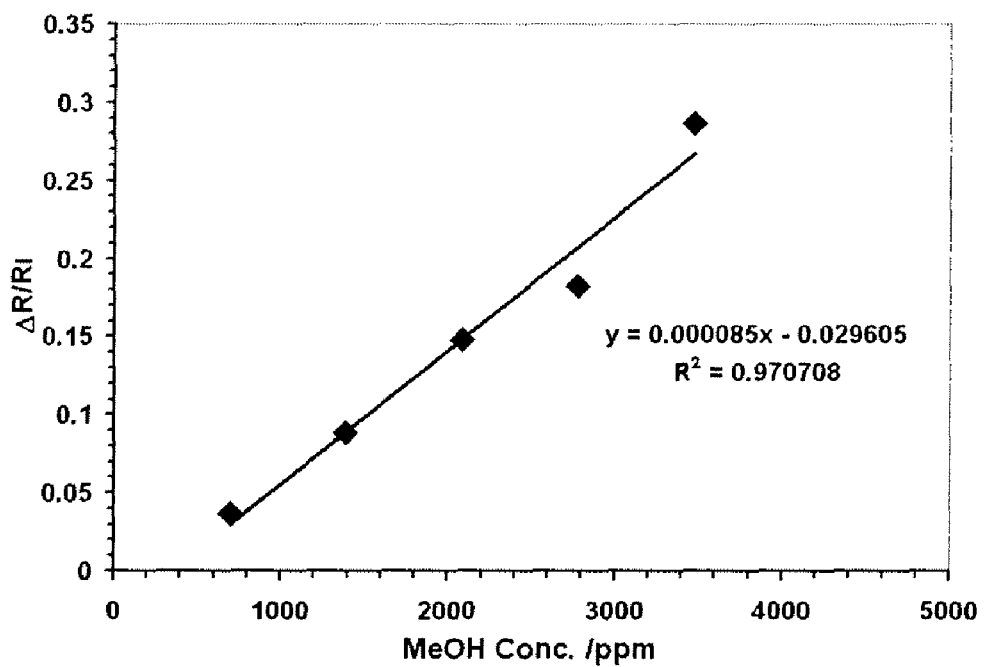

FIGS. 7A and 7B are graphs showing a typical response of the chemical sensor of the present invention. FIG. 7A specifically shows a response profile of a fiber mat of PMMA+8% SWCNTS to methanol (MeOH) and hexane (Hx). These results indicate that a response time for the nanofiber sensor of the present invention (from baseline to resistance increase) is less than 30 seconds. FIG. 7A specifically shows the high selectivity of the polymer and SWCNTs composite nanofiber sensor of the present invention, as the response methanol is many times more sensitive than the response to hexane. FIG. 7B specifically shows the relative differential resistance change $\Delta R/R_i$ Vs for a methanol vapor concentration.

The use of nanofibers in the present invention is particularly beneficial in that it increases the sensitivity and decreases the response time of the sensor due to the high surface area of the fibers and the resultant porous nanofiber structure (these effects are enhanced if nanofibers are used). The use of nanofibers is cost effective due to the low cost and low quantity of materials when nanofibers are used. Further, the use of nanofibers facilitates miniaturization of the sensor system due to the high sensitivity of nanofibers owing to their high surface area. Also unlike polymer films, the nanofiber mats of the present invention are permeable to gases and their use can allow sensors that can be incorporated into filters.

These results show the ability of the sensors of the present invention to respond rapidly to changing concentrations of a VOC in the gaseous environment. Furthermore, the fast response time in detection is complemented by a fast recovery time back to nearly the baseline level prior to any VOC exposure.

In one embodiment of the present invention, chemical reactants are included in the nanofibers that can react with the sorbed VOCs or gases in the fiber. In these instances, the product of the reactant interacts with the polymer itself (or other inclusions present in the nanofiber) to dramatically increase its conductivity. For instance, organic and inorganic iodine compounds that will react with ozone and generate iodine (such as potassium iodide) can be used in one embodiment as the reactant in a PMMA/fullerene or a PMMA/SWCN nanofiber system intended for ozone detection. Iodine is liberated in the reaction with ozone and combines with the fullerene or the SWCN to form an intercalated complex that has a dramatically increased electrical conductivity. Another embodiment of the present invention utilizes conducting polymers or conventional polymers that have unsaturated C=C double bonds that will be oxidized by ozone, leading to the cleavage of the double bond and change the electron delocalization and induce a decreased conductivity of the material.

Other reagents that react rapidly with ozone can also be used and serve to modify the conductivity of the polymer to different extents. The reactants can be included in a conducting polymer nanofiber or in a conventional polymer nanofiber that is rendered electrically conductive by the addition of some form of carbon. The approach utilizes a chemical change in the fiber matrix as opposed to a reversible physical change; therefore the fiber matrix will slowly deteriorate with reaction and will eventually need to be replaced. In some instances with other reagent/reactant systems, a reversible reaction that regenerates the reactant is possible.

In one embodiment of the present invention, the above-noted fibers or constituents included in them, designed to undergo a chemical reaction to modify their electrical conductivity, are part of a disposable fiber sensor element which could be replaced on an electronics unit detecting for example ozone. Accordingly, in this embodiment, a user would after exposure and/or warning of exposure, install a new fiber sensor element before re-entering an environment subject to ozone exposure. Alternatively, the lifetime of the chemical reaction and the concomitant conductivity change would be predetermined ahead of time, and the electronics unit would inform the user of the exposure sensitivity remaining on the sensor.

In another embodiment of the present invention, the fiber sensor and electronics unit are disposable.

Figure 8:
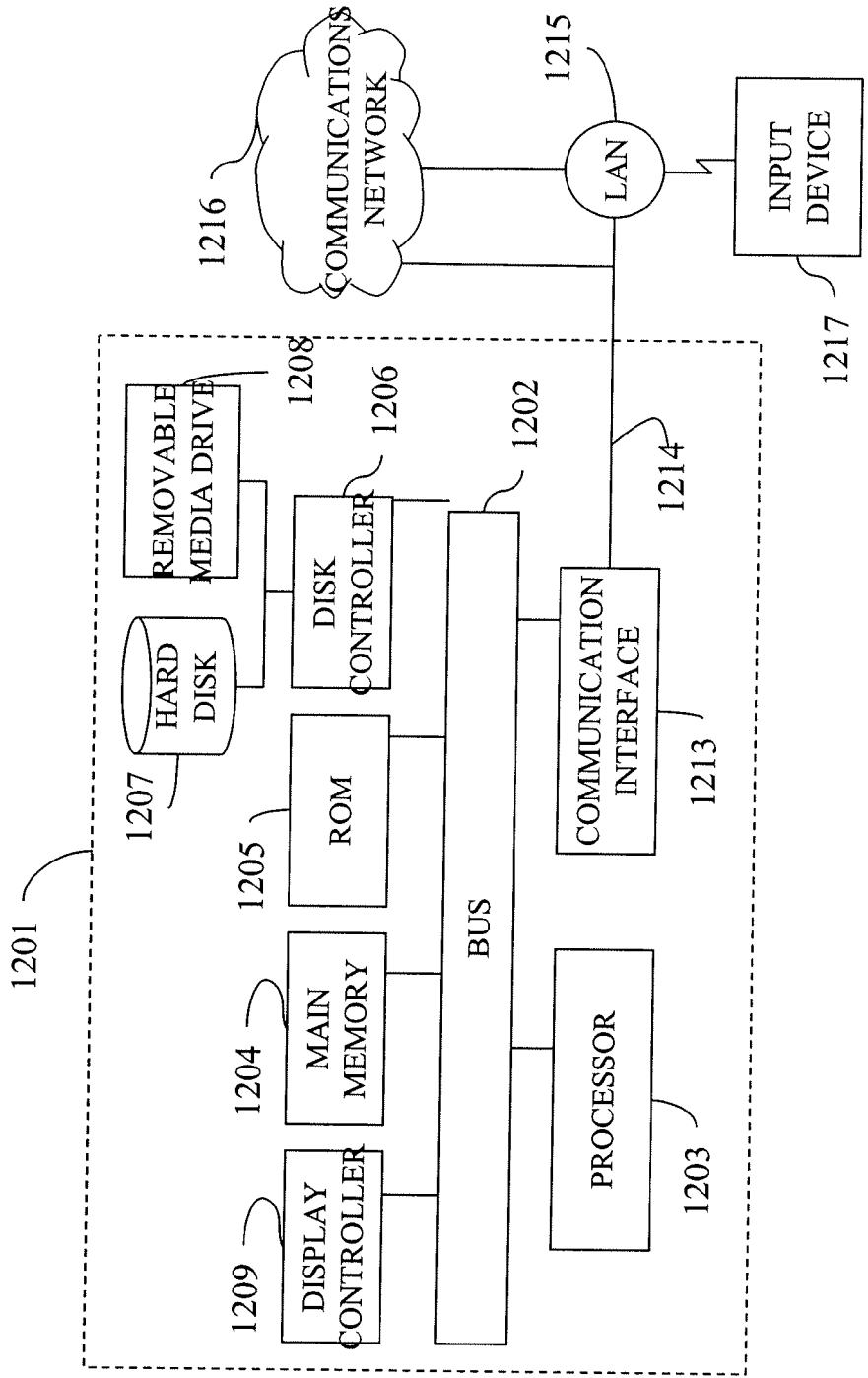
FIG. 8 is a schematic illustration showing computer system according to one embodiment of the present invention.

FIG. 8 is illustrates one embodiment of a computer system 1201 in which the analyzer 18 of the present invention can be implemented. The computer system 1201 is programmed and/or configured to perform any or all of the functions described above. In particular, the computer system depicted in FIG. 8 is capable of executing a number of programs designed to implement a "finger print" recognition of the sensor signature based on learned responses in which known volatile species are catalogued. The computer system depicted in FIG. 8 can then, based on these learned responses, embodied for example in analyzer 18 of the present invention can determine if the observed response matches a particular species of interest, and based on the magnitude of the response determine a concentration level of the species.

U.S. Pat. Nos. 6,680,206 and 6,289,328 (the entire contents of which are incorporated herein by reference) provide details on the development of a system to learn respective responses, as would be applicable in the present invention for particular VOC and fiber-types chosen.

The computer system depicted in FIG. 8 may be in communication with other processors and computers via the communications network 1216 (discussed below). The computer system 1201 includes a bus 1202 or other communication mechanism for communicating information, and a internal processor 1203 coupled with the bus 1202 for processing the information. The computer system 1201 includes a memory 1204, such as a random access memory (RAM) or other dynamic storage device (e.g., dynamic RAM (DRAM), static RAM (SRAM), and synchronous DRAM (SDRAM)). The computer system 1201 preferably includes a non-volatile memory such as for example a read only memory (ROM) 1205 or other static storage device (e.g., programmable ROM (PROM), erasable PROM (EPROM), and electrically erasable PROM (EEPROM)).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)) that are especially designed to process analog signals and convert the analog signals to the digital domain.

The computer system 1201 also includes a communication interface 1213 coupled to the bus 1202. The communication interface 1213 provides a two-way data communication coupling to a network link 1214 that is connected at least temporarily to, for example, a local area network (LAN) 1215, or to another communications network 1216 such as the Internet during downloading of software to the processor 24. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented as part of the communication interface 1213 to provide data exchange. In any such implementation, the communication interface 1213 sends and receives electrical, electromagnetic or optical signals that carry digital data streams representing various types of information. Such communications are applicable in various of the embodiments of the present invention, where the analyzer 18 is linked to network resources for example permitting data files and program resources to be shared. Moreover, the analyzer 18 may be in communication with other analyzers forming a network of sensors monitoring for chemical species. Moreover, the analyzer 18 may be in communication with global positioning satellite (GPS) information for cases where the sensor of the present invention is on a mobile platform.

Indeed, in one embodiment of the present invention there is provided a network of sensors, as shown for example in FIG. 9. One example could be a network of building alarm system. Each individual room is equipped with a chemical sensor of the presnt invention. When there is toxic gas at alarm level has been detected, the chemical sensor will send out alarm signal to the main control unit, then trigger the building alarm system. FIG. 9 is a schematic illustration showing a network 100 of chemical sensors according to one embodiment of the present invention. In this illustration, multiple sensors (ie., a network) are placed at distinct sites 110, 112, 114, and 116 (for example in different rooms in a building). The sensors are connected by a network (such as the LAN 1215 shown in FIG. 8) to a main control 118. The main control 118 can be configured to activate alarm 120 should the concentration of VOCs exceed a predetermined threshold.

In one embodiment of the present invention, the network can continuously monitor for example a sensor array conductivity profile and respond to specific pre-identified trigger patterns by implementing second level sensors to confirm the presence of volatile or remotely implement mitigation tasks. Mitigation tasks can range from identification of concentration profiles for the suspect VOC to control of robotic equipment to mitigate threat.

In one embodiment of the present invention, chemical sensors utilizing the features described above can be integrated with robotics 122 to produce chemotactic devices that are cable of following a plume or seek the origin of specific odorants in a geographic region. Such sensors and others described above in the various embodiments of the present invention can be provided with integrated electronic components permitting continuous monitoring of a sensor conductivity profile in order to respond to specific pre-identified trigger patterns, allowing for rapid detection of chemical species. The integrated electronics can include a wireless communication module (such as for example the communication interface 1213 and the network link 1214 in FIG. 8) to form a distributed network of sensors.

In other application areas, the ability of the present invention to print electrodes in fabrics and to electrospin appropriate fibers with the printed electrodes permits in one embodiment of the present invention the construction of wearable sensors.

Such wearable sensors have a variety of applications from sensors in health care patients where the sensors are on wound dressings, thereby permitting the recording over time the progress of patient in recovery from open wounds where infections may develop. The sensors would be connected to a remote diagnostic system for acquisition, processing, and control of the sensor.

Other applications include for example wearable sensors on the attire of miners working in closed spaces and susceptible to exposure to explosive or toxic gases.

Numerous modifications and variations of the present invention are possible in light of the above teachings. It is therefore to be understood that within the scope of the appended claims, the invention may be practiced otherwise than as specifically described herein.

The invention claimed is:

1. A chemical sensor comprising:
   a plurality of fibers whose electrical impedance varies upon exposure to a chemical species;
   a substrate supporting and electrically isolating the fibers; and
   a set of electrodes disposed on the plurality of fibers at spatially separated points to permit the electrical impedance of the plurality of fibers to be measured.

2. The sensor of claim 1, wherein the fibers comprise nanofibers whose average fiber diameter is less than 500 nm.

3. The sensor of claim 1, wherein the fibers comprise nanofibers whose average fiber diameter is less than 100 nm.

4. The sensor of claim 1, wherein the fibers have an electrical impedance which changes due to at least one of an increase in volumetric size of the fibers by sorption of the chemical species or a change in electrical conduction by a chemical reaction or sorption of the chemical species with a material of the fiber.

5. The sensor of claim 1, wherein the fibers comprise conductive fibers.

6. The sensor of claim 5, wherein:
   the conductive fibers comprise a non-conducting medium and a conducting additive dispersed in the non-conducting medium, and the conducting additive has a concentration which permits electrical conduction by percolation of charge carriers through the conductive fibers.

7. The sensor of claim 6, wherein the conducting medium comprises a percentage of the conductive fibers ranging from 2% to 10%.

8. The sensor of claim 6, wherein the conducting medium comprises carbon tubes.

9. The sensor of claim 8, wherein the carbon tubes are disposed in a body of the fibers at a concentration that is within 10% of a conduction percolation threshold.

10. The sensor of claim 6, wherein the non-conducting medium comprises an organic polymer.

11. The sensor of claim 1, wherein the fibers comprises conductive particles included in the fibers to increase a fiber conductivity.

12. The sensor of claim 11, wherein the conductive particles include at least one of carbon black, carbon nanotubes, fullerenes and conducting metals, including at least one of Ag, Au, Cu, and Al.

13. The sensor of claim 1, wherein the plurality of fibers comprises aligned fibers.

14. The sensor of claim 1, further comprising:
   plural sets of the electrodes to which respective groups of the fibers are connected at spatially separated points.

15. The sensor of claim 1, further comprising:
   a preconcentrator disposed in relation to the plurality of fibers to enhance sorption of the chemical species.

16. The sensor of claim 15, wherein the preconcentrator comprises a silicone layer.

17. A system for sensing a chemical species, comprising:
   a chemical sensor including,
   a plurality of fibers having a electrical impedance which varies upon exposure to the chemical species,
   a substrate supporting and electrically isolating the fibers, and
   a set of electrodes disposed on the plurality of fibers at spatially separated points on the fibers;
   an impedance measuring device coupled to the electrodes and configured to determine an electrical impedance of the plurality of fibers, and
   an analyzer configured to identify the chemical species based on a change in the electrical impedance.

18. The system of claim 17, wherein the fibers comprise nanofibers having an average fiber diameter less than 500 nm.

19. The system of claim 17, wherein the fibers comprise nanofibers having an average fiber diameter less than 100 nm.

20. The system of claim 17, wherein the fibers have an electrical impedance which changes due to at least one of an increase in volumetric size of the fibers by sorption of the chemical species, a change in electrical conduction by a chemical reaction of the chemical species with a material of the fiber or surface adsorption of a volatile solvent on a surface of the fiber.

21. The system of claim 17, wherein the fibers comprise conductive fibers.

22. The system of claim 21, wherein:
   the conductive elements comprise a conducting additive dispersed in the non-conducting medium, and
   the conducting additive has a density which permits electrical conduction by percolation of charge carriers through regions of the conducting medium in the conductive fibers.

23. The system of claim 22, wherein the conducting medium comprises a percentage of the conductive fibers ranging from 2% to 10%.

24. The system of claim 22, wherein the conducting medium comprises carbon nanotubes.

25. The system of claim 24, wherein the carbon nanotubes are disposed in a body of the fibers at a concentration that is within 10% of a conduction percolation threshold.

26. The system of claim 22, wherein the fibers comprises conductive particles included in the fibers to increase a fiber conductivity.)

27. The system of claim 26, wherein the conductive particles include at least one of carbon black, carbon nanotubes, fullerenes and conducting metals, including at least one of Ag, Au, Cu, and Al.

28. The system of claim 22, wherein the non-conducting medium comprises an organic polymer.

29. The system of claim 17, wherein the plurality of fibers comprises aligned fibers.

30. The system of claim 17, further comprising:
   plural sets of electrodes connected to plural respective groups of the fibers at spatially separated points.

31. The system of claim 17, further comprising a plurality of the chemical sensors forming a sensor network.

32. A method for sensing a chemical species, comprising:
providing a chemical sensor disposed on a gas or liquid permeable substrate;
exposing the chemical sensor disposed on the gas or liquid permeable substrate to the chemical species in a gaseous or liquid environment;
measuring at least one change in an electrical impedance between spatially separated electrodes disposed on a plurality of fibers of the chemical sensor upon exposure of the fibers to the chemical species; and
identifying the chemical species based on the measured change in the electrical impedance of the plurality of fibers.

33. The method of claim 32, wherein measuring comprises:
measuring the change in electrical impedance of a plurality of nanofibers having an average fiber diameter less than 500 nm.

34. The method of claim 32, wherein measuring comprises:
measuring the change in electrical impedance of a plurality of nanofibers having an average fiber diameter less than 100 nm.

35. The method of claim 32, wherein measuring comprises:
measuring the change in electrical impedance of a plurality of conductive fibers.

36. The method of claim 32, wherein measuring comprises:
measuring the change in electrical impedance of a plurality of fiber having a non-conducting medium and a conducting medium dispersed in the non-conducting medium,
wherein the conducting medium has a density which permits electrical conduction by percolation of charge carriers through regions of the conducting medium in the conductive fibers.

37. The method of claim 32, wherein identifying the chemical species comprises:
comparing the measured change in electrical impedance to a library of changes for known concentrations of predetermined chemical species.

38. The method of claim 32, wherein identifying the chemical species comprises:
comparing measured changes in electrical impedance for respective groups of fibers to a library of changes for known concentrations of plural predetermined chemical species.

39. The method of claim 32, wherein measuring comprises measuring changes due to at least one of an increase in volumetric size of the fibers by sorption of the chemical species or a change in electrical conduction by a chemical reaction of the chemical species with a material of the fiber.

40. The method of claim 32, wherein the liquid environment is aqueous.

41. The sensor of claim 16, wherein the silicone layer comprises a silicone elastomer or PDMS film.)

42. The sensor of claim 1, wherein the fibers comprise a polymer blended fiber spun from a common solvent.

43. The sensor of claim 1, wherein the fibers comprise conductive fibers.

44. The sensor of claim 1, wherein the fibers are composed of at least one polymer that is conductive and at least one polymer that is nonconductive.

45. The sensor of claim 1, wherein:
the electrical impedance varies upon exposure to an organic species in response to concentrations of the organic species in the parts per million range or greater; and
the substrate comprises a gas or liquid permeable substrate supporting and electrically isolating the fibers
a plurality of fibers whose electrical impedance varies upon exposure to a chemical species;
a substrate supporting and electrically isolating the fibers; and
a set of electrodes disposed on the plurality of fibers at spatially separated points to permit the electrical impedance of the plurality of fibers to be measured.

46. The sensor of claim 45, wherein the chemical sensor functions as a residual lifetime indicator for a filter.

47. The sensor of claim 45,
wherein
the fibers comprise a non-conducting medium and an elongated conducting additive dispersed in the non-conducting medium comprising a 1-30 weight percentage.

48. The sensor of claim 47, wherein the elongated conducting additive comprises carbon nanotubes.

49. A system for sensing a chemical species,
a chemical sensor including,
a plurality of fibers having an electrical impedance which varies upon exposure to a chemical species,
a substrate supporting and electrically isolating the fibers,
a set of electrodes connected to the plurality of fibers at spatially separated points to permit the electrical impedance of the plurality of fibers to be measured, and
said fibers having an electrical impedance which changes due to a change in electrical conduction by a chemical reaction of the chemical species with a material of the fiber; and
a source of the chemical species which chemically reacts with the material of the fiber to chemically alter the bonds of the material of the fiber after exposure to the chemical species.

50. The sensor of claim 1, wherein the electrodes are printed on the plurality of fibers.

51. The system of claim 17, wherein the electrodes are printed on the plurality of fibers.

52. A chemical sensor comprising:
a plurality of fibers whose electrical impedance varies upon exposure to a chemical species;
a flexible, gas or liquid permeable substrate supporting and electrically isolating the fibers; and
a set of electrodes in electrical contact with the plurality of fibers at spatially separated points to permit the electrical impedance of the plurality of fibers to be measured,
wherein the electrodes are disposed on the plurality of fibers.

53. The sensor of claim 52, wherein
the fibers comprise a non-conducting medium and an elongated conducting additive dispersed in the non-conducting medium, and
the elongated conducting additive has a density which permits electrical conduction by percolation of charge carriers through the conductive fibers.

54. The sensor of claim 53, wherein the elongated conducting additive comprises carbon nanotubes.

55. The sensor of claim 52, wherein chemical species chemically react with the material of the fiber to chemically alter the bonds of the material of the fiber after exposure to the chemical species.

56. The sensor of claim 52, wherein the electrodes are printed on the plurality of fibers.

57. The sensor of claim 52, wherein the electrodes are disposed on the substrate.

* * * * *